United States Patent
Ruddle et al.

(10) Patent No.: US 8,128,401 B2
(45) Date of Patent: Mar. 6, 2012

(54) CANNULA FOR A COMBINED DENTAL IRRIGATOR AND VACUUM DEVICE

(75) Inventors: Clifford J. Ruddle, Santa Barbara, CA (US); Stephen Barker, Santa Barbara, CA (US)

(73) Assignee: Clifford J. Ruddle, Santa Barbra, CA (US)

(*) Notice: Subject to any disclaimer, the term of this patent is extended or adjusted under 35 U.S.C. 154(b) by 45 days.

(21) Appl. No.: 11/618,271

(22) Filed: Dec. 29, 2006

(65) Prior Publication Data

US 2008/0160480 A1    Jul. 3, 2008

(51) Int. Cl.
*A61C 17/00* (2006.01)
*A61C 5/02* (2006.01)
*A61C 17/06* (2006.01)

(52) U.S. Cl. .................................. 433/81; 433/91

(58) Field of Classification Search .............. 433/81–82, 433/89–9, 215, 224, 90, 91, 29; 604/38, 604/19, 30, 35, 22, 40, 131, 134, 153, 181, 604/187, 185, 191, 235, 533–284, 158–163, 604/118–121, 239–243; 601/163–165; 285/401, 285/402, 376

See application file for complete search history.

(56) References Cited

U.S. PATENT DOCUMENTS

| | | | | |
|---|---|---|---|---|
| 3,871,099 A * | 3/1975 | Kahn | | 433/224 |
| 4,109,653 A * | 8/1978 | Kozam et al. | | 604/191 |
| 4,276,880 A | 7/1981 | Malmin | | |
| 4,504,264 A * | 3/1985 | Kelman | | 604/22 |
| 4,842,581 A * | 6/1989 | Davis | | 604/38 |
| 4,983,160 A * | 1/1991 | Steppe et al. | | 604/22 |
| 5,279,542 A * | 1/1994 | Wilk | | 604/19 |
| 6,319,001 B1 * | 11/2001 | Esrock | | 433/80 |
| 6,422,865 B1 * | 7/2002 | Fischer | | 433/81 |
| 6,638,064 B1 * | 10/2003 | Nance | | 433/81 |
| 6,676,677 B2 * | 1/2004 | Klein | | 606/171 |
| 2002/0142260 A1 * | 10/2002 | Pond | | 433/81 |
| 2002/0161326 A1 * | 10/2002 | Sussman et al. | | 604/35 |
| 2004/0110112 A1 * | 6/2004 | Xie et al. | | 433/89 |

FOREIGN PATENT DOCUMENTS

| | | |
|---|---|---|
| JP | 2004313659 A | 11/2004 |
| WO | 2005122943 A | 12/2005 |

OTHER PUBLICATIONS

European Search Report from corresponding European Application No. 07124000.6, mailed Apr. 18, 2008.

* cited by examiner

*Primary Examiner* — Todd Manahan
*Assistant Examiner* — Yogesh Patel
(74) *Attorney, Agent, or Firm* — Polster Lieder Woodruff & Lucchesi, L.C.

(57) ABSTRACT

A cannula assembly is removably mountable to a syringe body having a pair of side-by-side chambers; there being an opening into each chamber at a bottom of the syringe. The cannula assembly includes a connector and a dual lumen assembly extending from the connector. The dual lumen assembly includes a pair of tubes defining two fluid paths. The connector includes fluid paths which, when the cannula assembly is mounted to the syringe, place the fluid path of one of the tubes in fluid communication with one of the syringe body chambers and the fluid path of the other of the dual lumen tubes in fluid communication with the other of the syringe body chambers.

28 Claims, 6 Drawing Sheets

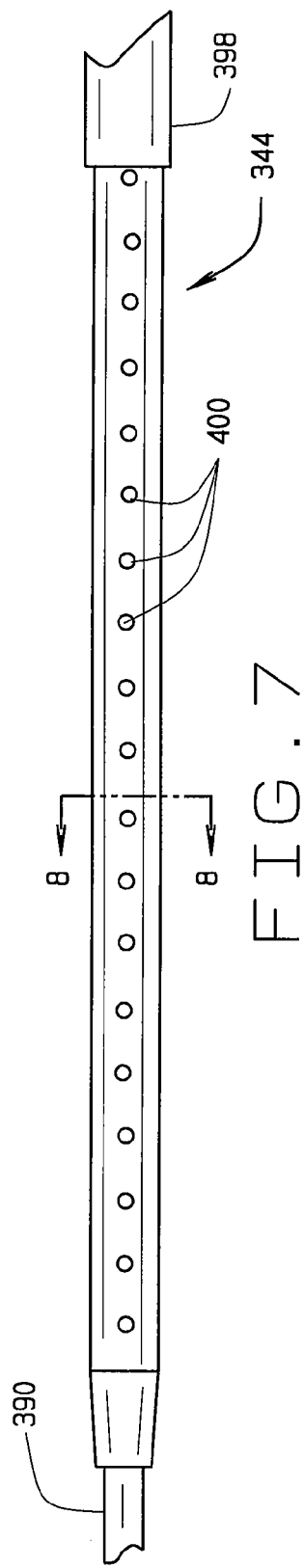
FIG. 7
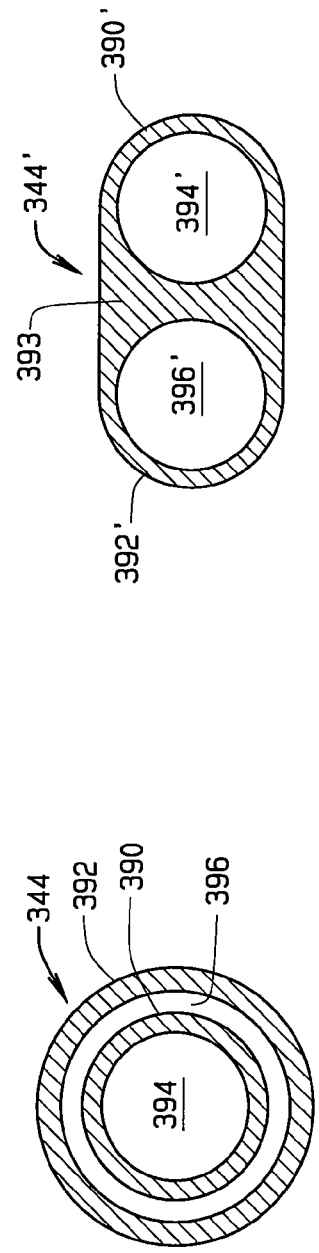
FIG. 9
FIG. 8
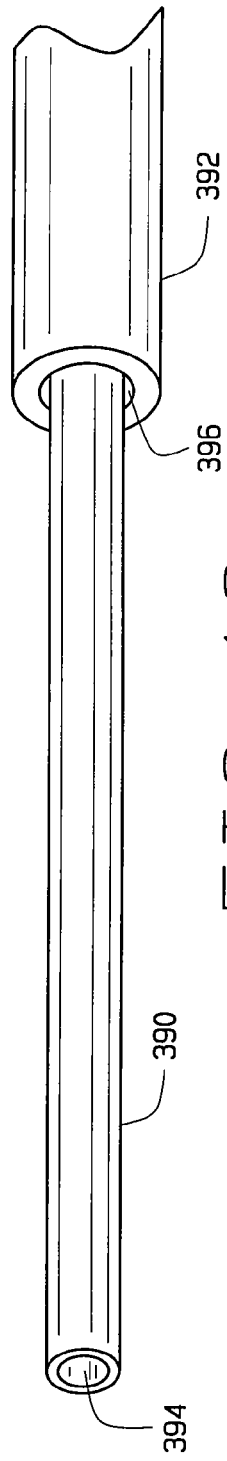
FIG. 10

CANNULA FOR A COMBINED DENTAL IRRIGATOR AND VACUUM DEVICE

CROSS-REFERENCE TO RELATED APPLICATIONS

This application is related to co-pending application Ser. No. 11/618,191 filed Dec. 29, 2006, entitled Syringe For A Combined Dental Irrigator And Vacuum Device, and which is incorporated herein by reference.

STATEMENT REGARDING FEDERALLY SPONSORED RESEARCH OR DEVELOPMENT

Not Applicable.

BACKGROUND OF THE INVENTION

This invention relates to endodontic tools, and in particular, to a cannula for a combined irrigator and vacuum device. Although the cannula and the combined irrigator/vacuum device to which it is connectable are described for use with endodontic procedures, it will be apparent that they can be used for other dental or medical procedures as well.

Following tooth maturation, the dental pulp is harbored within the structural elements of the tooth. Frequently, and for a variety of reasons, the pulp is irreversibly injured, resulting in inflammatory and infectious conditions which often adversely affect the tooth and its supporting structures. Clinically, as an alternative to extraction, root canal treatment is performed and ideally is directed towards the elimination of pulp, bacteria, and related irritants from the root canal system, followed by three-dimensionally filling the root canal space with an inert, biocompatible, dimensionally stable, filling material, such as gutta percha. Ideally, the obturation procedures will fill not just the main canal, but the fins, webs, anastomoses, lateral canals, and all portals of exit between the root canal system and the tooth's attachment apparatus.

Central to a successful endodontic (or root canal) treatment has been the use of chemical reagents during mechanical root canal shaping procedures to completely clean all aspects of the root canal system. The chemicals used to enhance canal debridement and disinfection during cleaning and shaping procedures potentially reach all aspects of the root canal system. The most popular chemicals currently used during canal preparation to actively assist in cleaning and disinfecting include bleach, hydrogen peroxide, and chelating agents. Clinicians irrigate with a 2%-5% solution of a clear, pale, greenish-yellow strongly alkaline solution of sodium hypochlorite (NaOCl), a 17% solution of and ethylenediaminetetracetic acid (EDTA), or other final rinse solutions. These solutions are used individually or in combination.

During canal preparation, a solution of NaOCl is liberally irrigated into the root canal space where its solvent action facilitates the digestion and removal of pulp, bacteria, viruses, spores, endotoxins and other irritants generated by microorganisms. This solution has the potential to circulate, penetrate and, hence, clean into all aspects of the root canal space. However, studies have shown that even the most thorough use of sodium hypochlorite does not remove all the material from the root canal. The walls of a root canal are comprised of dentin, which structurally contains thousands of dentinal tubules per square millimeter. Instruments used to cut dentin and shape a canal, in combination with organic substrates, forms a cocktail of debris. Dentinal mud, pulpal tissue, bacteria, and other related irritants have been consistently visualized histologically in the dentinal tubules and various aspects of the root canal systems following root canal preparation procedures. Thus, after shaping procedures, the root canal is frequently covered with a film of debris, described and referred to in the literature as a "smear layer." Recently, biofilms have been reported within the environment of the root canal space. Biofilms form from a gelatin-like, sticky polysaccharide mass and harbor bacteria. As such, cleaning refers to those clinical procedures that encourage debridement, removal of the smear layer, and the elimination of biofilms.

After cleaning and shaping, the root canal has been traditionally filled with gutta percha and a sealer. Failure to adequately clean the root canal system can compromise the filling and sealing of the root canal system. If obturation is incomplete then the root canal space is predisposed to bacterial leakage and failure. Post-treatment failures attributable to leakage are common and require endodontic retreatment of the tooth or extraction. Therefore, to improve clinical success, irrigating methods must be developed to promote safe and three-dimensional cleaning of a complex anatomical space. Certainly, one of the most intriguing frontiers of complete endodontic cleaning is the reagents, their delivery, and their method of activation.

Flushing of the root canal is generally accomplished with an irrigating syringe which is utilized to inject fluids, as mentioned above, into the root canal space. During the cleaning process, dentinal debris, pulpal tissue, bacteria when present, and their related irritants are moved into solution during the preparation of any given root canal. As can be appreciated, this dirty solution must be removed from the root canal as part of the cleaning process, and prior to filling and sealing of the prepared root canal. Removal of the solution is typically accomplished with a vacuum which is separate from the irrigating syringe. The definitive drying of the preparation is accomplished by wicking residual moisture from the canal using appropriately sized paper points. However, in the time that it takes to switch from the irrigating syringe to the vacuum device, debris, bacteria, and other elements that the practitioner desires to remove oftentimes settle back into the canal, making removal of this debris more difficult.

BRIEF SUMMARY OF THE DISCLOSURE

Briefly stated, a cannula assembly is provided for an irrigation/vacuum syringe. The irrigator/vacuum syringe comprises a hollow body having a body wall, a body bottom and a divider in the body which divides the hollow body into a first (clean or fresh fluid) chamber and a second (waste fluid) chamber within the body. The syringe body includes a first chamber opening in the body bottom in the first chamber and a second chamber opening in the body bottom in the second chamber. The first and second chamber openings are spaced apart from each other;

The cannula assembly is removably connectable to the syringe body. The cannula assembly includes a connector and a flexible lumen. The connector comprises an upper surface, a side wall and a lower surface. A waste fluid flow path and a fresh fluid flow path are formed in the connector. The waste and fresh fluid flow paths extend from the connector upper surface and open at the connector upper surface.

In an illustrative embodiment, the connector comprises a connector body and a connector cover. The connector body has an upper surface and a lower surface. The fresh fluid and waste fluid flow paths comprise a first connector passage and a second connector passage, respectively, which are formed in the connector body and are generally parallel to each other. A bore is formed in the connector body lower surface and an opening is formed in a top surface of the bore to place the bore in communication with the second connector passage. The first connector passage extends through a wall of the connector body from the connector body upper surface to the connector body lower surface.

The connector cover comprises a lower surface of the connector, a cover peripheral wall extending around the connector lower surface, and a post extending upwardly from the connector lower surface. The post includes an axial connector passage and a laterally extending bore. The laterally extending bore extends from a surface of the post to the axial connector passage in the post. The cover post and connector body bottom bore in combination define an annular chamber with which the connector first passage is in communication.

The lumen comprises a tube which is placed in communication with the waste fluid flow path and the fresh fluid flow path. When the cannula assembly is mounted to the syringe, the fresh fluid flow path is in fluid communication with the first (fresh fluid) chamber of the syringe and the waste fluid flow path is in fluid communication with the second (waste fluid) chamber of the syringe. In one embodiment, the lumen is a single tube lumen which can be placed in communication with either or both of the fresh and waste fluid flow paths. If it is in communication with both the fresh fluid and waste fluid flow paths, the connector can be provided with one-way valves.

In a second embodiment, the lumen is a dual tube lumen and comprises a first tube defining a first lumen passage and a second tube defining a second lumen passage. The first lumen passage and the second lumen passage are in fluid communication with the fresh fluid flow path and the waste fluid flow path, respectively. The first lumen passage has an exit proximate a free or distal end of the first tube and the second lumen has an entrance proximate a free or distal end of the second tube. The exit allows fluid to exit from the cannula assembly to deliver fluid to a root canal and the entrance allows fluid to enter the cannula assembly to allow fluid to be removed from a root canal. The first and second lumen passages can be coaxial, in which case, the first lumen passage defines an outer passage and the second lumen passage defines an inner passage. Whether the first and second lumen passages are coaxial or side-by-side, the entrance and exit can be spaced axially from each other. In this instance, the second tube is longer than the first tube to space the entrance of the second tube below the exit of the first tube.

The cannula assembly first tube can be provided with a plurality of pores on a wall of the tube. In this instance, the first tube can be sealed at a bottom thereof, such that fluid can only exit the tube through the pores.

The irrigator/vacuum syringe includes a nose extending from the body bottom and a collar surrounding the nose. The nose and collar define an annular channel. The nose is generally centered relative to the body bottom and includes a passage therethrough defining the second chamber opening. The first chamber opening is positioned in the body bottom between the nose and the collar. The first connector passage is defined by an annular wall sized and shaped to fit about the syringe nose and to be received in the syringe annular channel.

BRIEF DESCRIPTION OF THE SEVERAL VIEWS OF THE DRAWINGS

FIG. 7 is an enlarged perspective view of a lumen of the cannula assembly;

FIG. 8 is a cross-sectional view of the lumen taken along line 8-8 of FIG. 7;

FIG. 9 is a cross-sectional view of an alternative embodiment of the lumen;

FIG. 10 is a perspective view of a distal end of the lumen; and

Corresponding reference numerals will be used throughout the several figures of the drawings.

DETAILED DESCRIPTION OF THE INVENTION

Figures 1, 2:
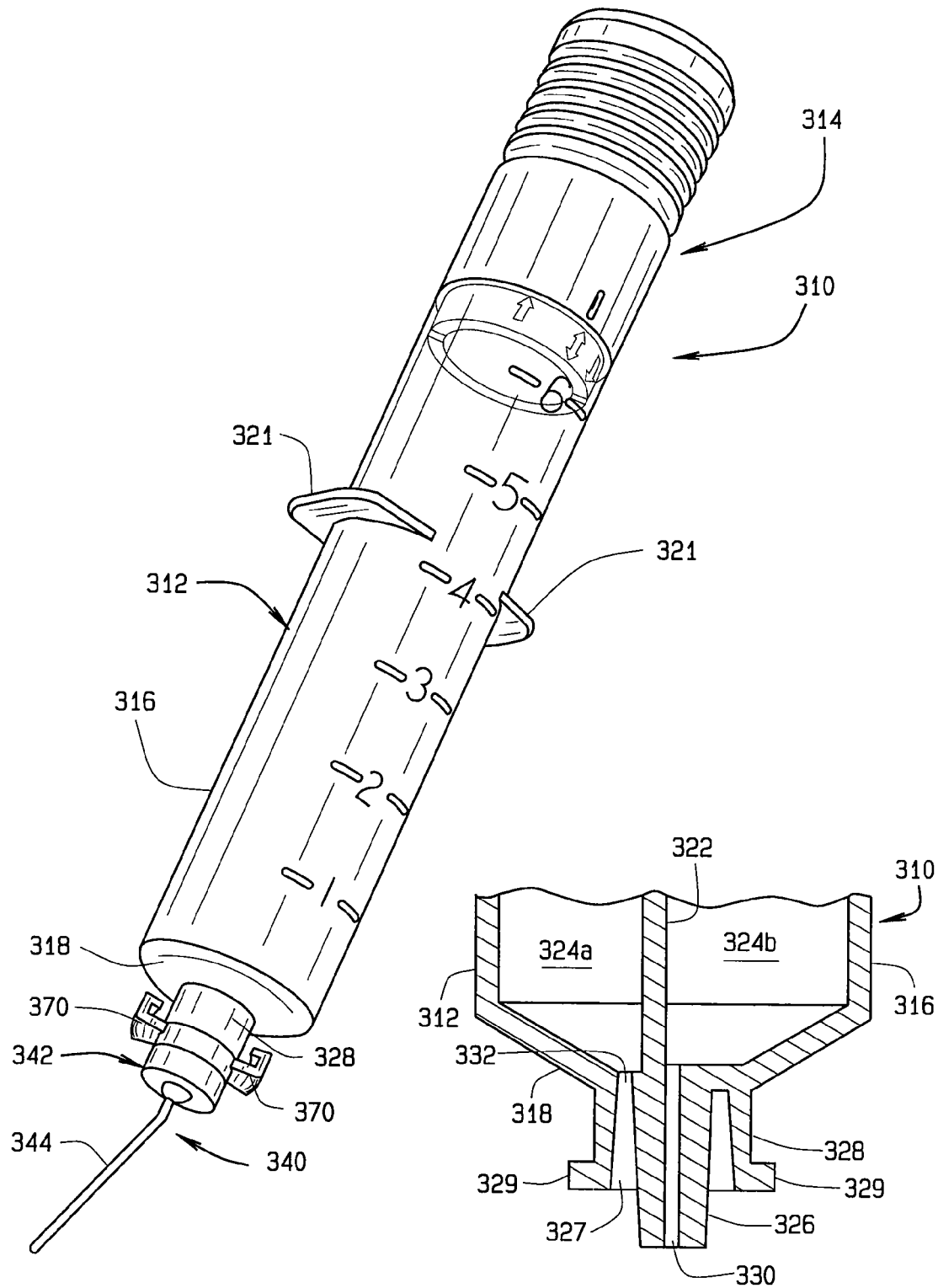
FIG. 1 is a perspective view of an illustrative combined irrigator/vacuum syringe with an illustrative embodiment of a lumen made in accordance with the invention.
FIG. 2 is an enlarged cross-sectional view of a bottom portion of the irrigator/vacuum syringe.
Figure 3:
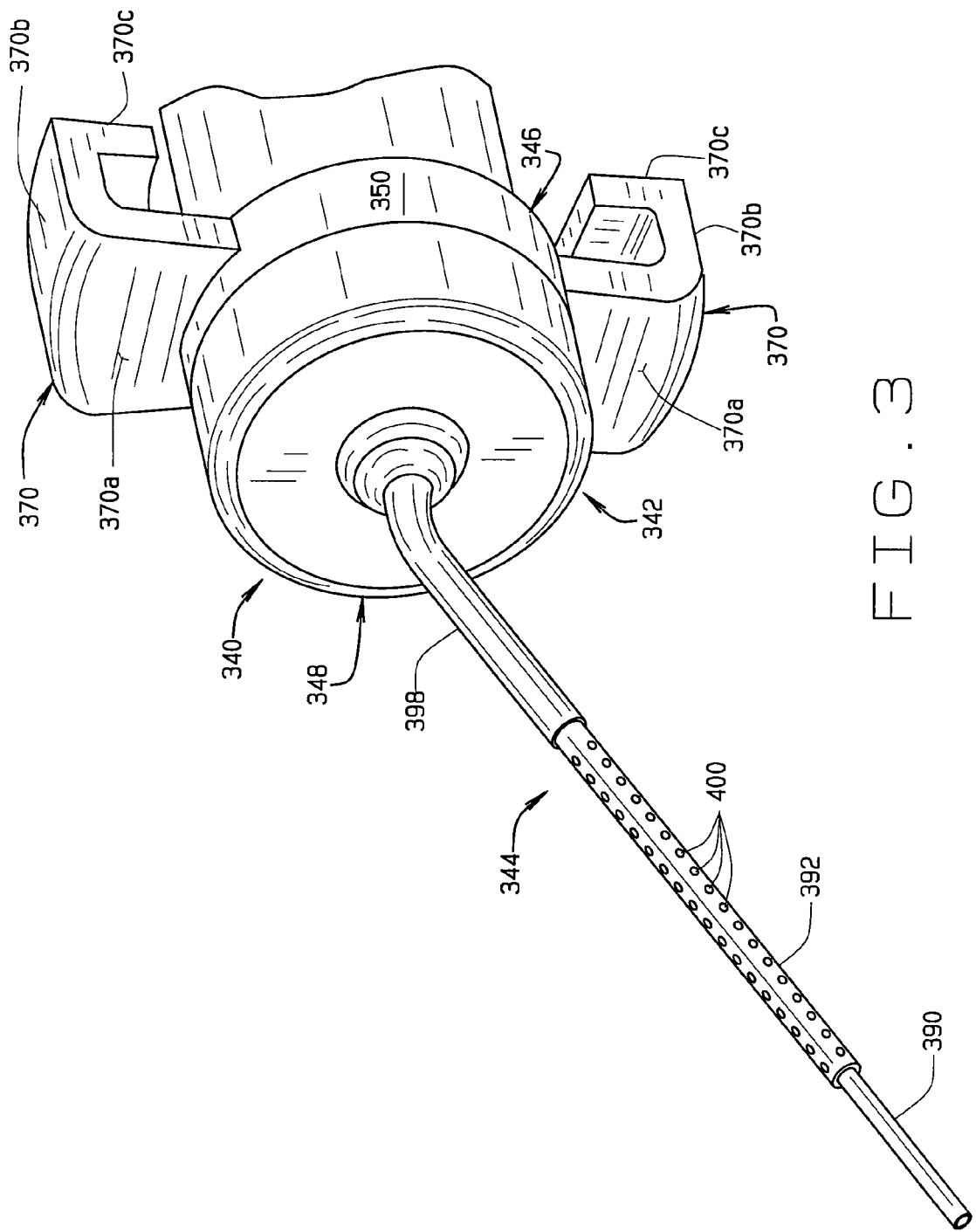
FIG. 3 is an enlarged perspective view of the cannula assembly which is removably mountable to the irrigator/vacuum syringe.
Figure 4:
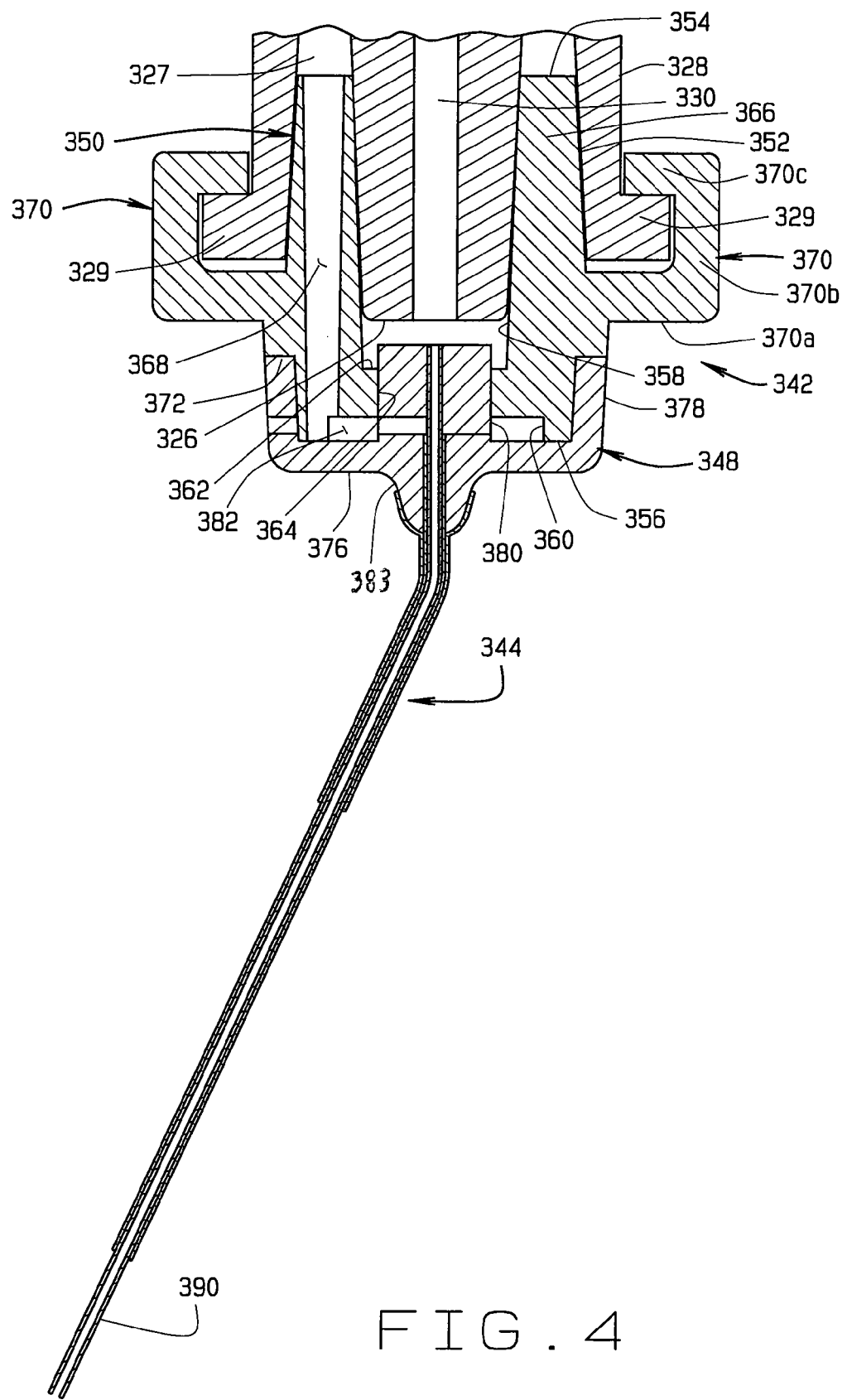
FIG. 4 is a cross-sectional view of the cannula assembly mounted to the irrigator/vacuum syringe.

The following detailed description illustrates the invention by way of example and not by way of limitation. This description will clearly enable one skilled in the art to make and use the invention, and describes several embodiments, adaptations, variations, alternatives and uses of the invention, including what we presently believe is the best mode of carrying out the invention. Additionally, it is to be understood that the invention is not limited in its application to the details of construction and the arrangements of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

An illustrative irrigator/vacuum syringe or device 310 is shown generally in FIG. 1 and enlarged in FIG. 2. The syringe 310 includes a hollow body 312 and a pump assembly 314. The body 312 includes a side wall 316, a bottom 318 and an open mouth or top end. The syringe 310 is shown in FIG. 1 to be generally circular, but can be any desired shape. Flanges 321 extend from opposite sides of the body wall 316 to facilitate use of the irrigator-vacuum syringe 310. Internally, the body 312 includes a separator 322 which divides the hollow body into two chambers 324a and 324b. Chamber 324a is a "clean" chamber which holds a supply of fresh irrigant and chamber 324b is a "waste" chamber which stores used irrigant which has been vacuumed from the root canal. As can be appreciated, the used or waste irrigant will contain all the elements which comprise the smear layer, as previously described.

As shown in FIG. 2, the irrigator-vacuum syringe 310 includes a central post or nose 326 extending from the bottom 318 of body 312. The nose 326 is surrounded by a collar 328, and hence the nose and collar, in combination, define an annular channel 327. Lugs 329 extend from opposite sides of the collar 328. The nose 326 is hollow, and defines a passage 330 which extends through the body bottom 318 and opens into the waste chamber 324b. A second opening 332 in the body bottom is positioned between the nose 326 and the collar 328 and opens into the clean chamber 324a, thereby placing the annular channel 327 in fluid communication with the clean chamber 324a.

As described in co-pending application Ser. No. 11/618,191, filed Dec. 29, 2006, entitled "Combined Dental Irrigator and Vacuum Device", which was published as US2008-0160479, and which is incorporated herein by reference, the pump assembly 314 is operable to selectively force fluid out of the clean chamber through the opening 332 at the base of the clean chamber and to vacuum fluid from a root canal into the waste chamber through the passage 330 in the nose 326.

So that the irrigation fluid contained in the clean chamber can be pumped into a root canal and so that used, spent, or "waste" irrigation fluid can be vacuumed out of the root canal, a cannula assembly 340 is provided which is removably mountable to the bottom end of the body 312 of the irrigator/vacuum syringe 310. The cannula assembly comprises a connector assembly 342 and a flexible one-piece dual lumen 344 which is connected to and extends from the connector assembly.

The connector assembly 342 comprises a connector body 346 and a connector cover 348. The connector body 346 comprises a generally cylindrical member 350 having an outer surface 352, an upper surface 354 and a lower surface 356. A central bore or chamber 358 extends downwardly from the upper surface 354. The bore 358 does not extend all the way through the member 350. A bottom bore 360 extends upwardly from the member lower surface 356. The bottom bore 360 is generally coaxial with the bore 358, but has a larger diameter than the bore 358. The bores 358 and 360 are separated by a wall 362 which forms a floor for the bore 358 and a ceiling for the bore 360. An opening 364 is formed in the approximate center of the wall 362 and extends through the wall 362 to place the bores 358 and 360 in communication with each other.

Figure 5:
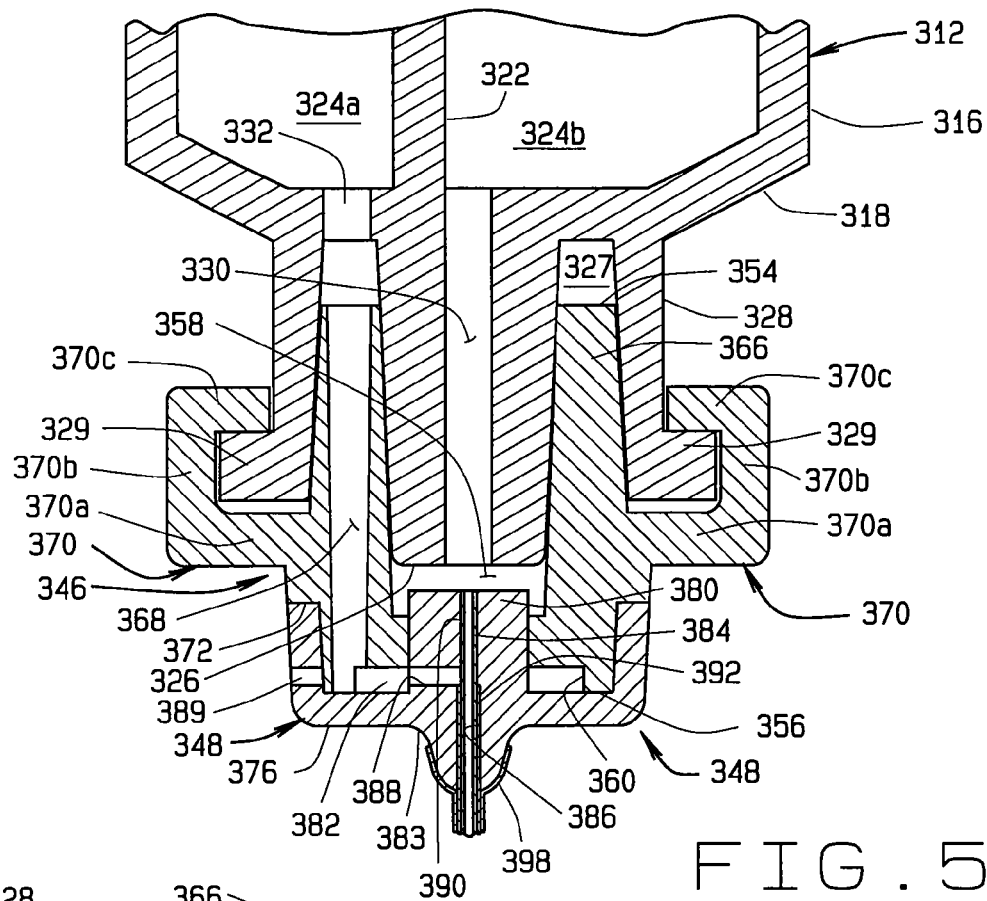
FIG. 5 is an enlarged cross-sectional view of the cannula assembly mounted to the irrigator/vacuum syringe.

The outer surface 352 of the body cylindrical member 350 is sized and shaped correspondingly to the inner surface of the collar 328 of the irrigator/vacuum syringe 310; and the central bore 358 has an inner surface sized and shaped correspondingly to the outer surface of the nose 326 of the irrigator/vacuum syringe 310. Hence, the outer surface 352 and the bore 358 of the body cylindrical member 350, in combination, define a generally annular wall 366 which is sized and shaped to be received in the annular channel 327 between the collar 328 and nose 326 of the irrigator/vacuum syringe 310. A second passage 368 extends through the annular wall 366 from the upper surface 354 to the lower surface 356. As seen in FIG. 5, the passage 368 opens into the bottom bore 360.

A pair of opposed fingers 370 extend outwardly from the outer surface 352 of the cylindrical member 350 approximately mid-way along the length of the cylindrical member 350. The fingers 370 each include a lower, generally horizontal portion 370a extending outwardly from the surface 352, a generally vertical portion 370b extending upwardly from the end of the portion 370a, and an upper generally horizontal portion 370c which extends inwardly toward the surface 352 from the end of the vertical portion 370b. The vertical portion 370b is spaced from the surface 352 by the lower horizontal portion 370a a distance slightly greater than the length of the lugs 329 and has a height slightly greater than the height of the lugs 329. The free end of the second horizontal portion 370c is spaced from the surface 352 by a distance at least equal to the annular width of the collar 328. As can be appreciated, the fingers 370 cooperate with the lugs 329 to hold the connector assembly 342 (and hence the cannula assembly 340) to the irrigator/vacuum syringe 310. A circumferential shoulder or step 372 is formed below the fingers 370.

The connector cover 348 comprises a bottom wall 376 and an outer peripheral wall 378. The wall 378 has a height approximately equal to the distance between the bottom of the shoulder 372 and the lower surface 356 of the connector body 346 and an inner surface shaped correspondingly to the outer surface 352 of the connector body cylindrical member 350 below the shoulder 372. A central post 380 extends upwardly from the upper surface of the bottom wall 376. The post 380 has an outer surface that is slightly inwardly sloped, giving the post a slightly trapezoidal shape. The post 380 has a height greater than the depth of the bottom bore 360 of the connector body and is sized and shaped to extend through the opening 364 in the bottom wall 362 of the connector body 346. Further, the post 380 is sized and shaped such that the outer surface of the post 380 will substantially seal against the surface of the connector body opening 364. When the cover 348 is mounted to the body 346, the post 380 and the body bore 360, in combination, define an annular channel 382. The connector cover 348 also includes a projection 383 extending from the outer or bottom surface of the connector cover bottom wall 376. The projection 383 is aligned with the post 380.

Figure 6:
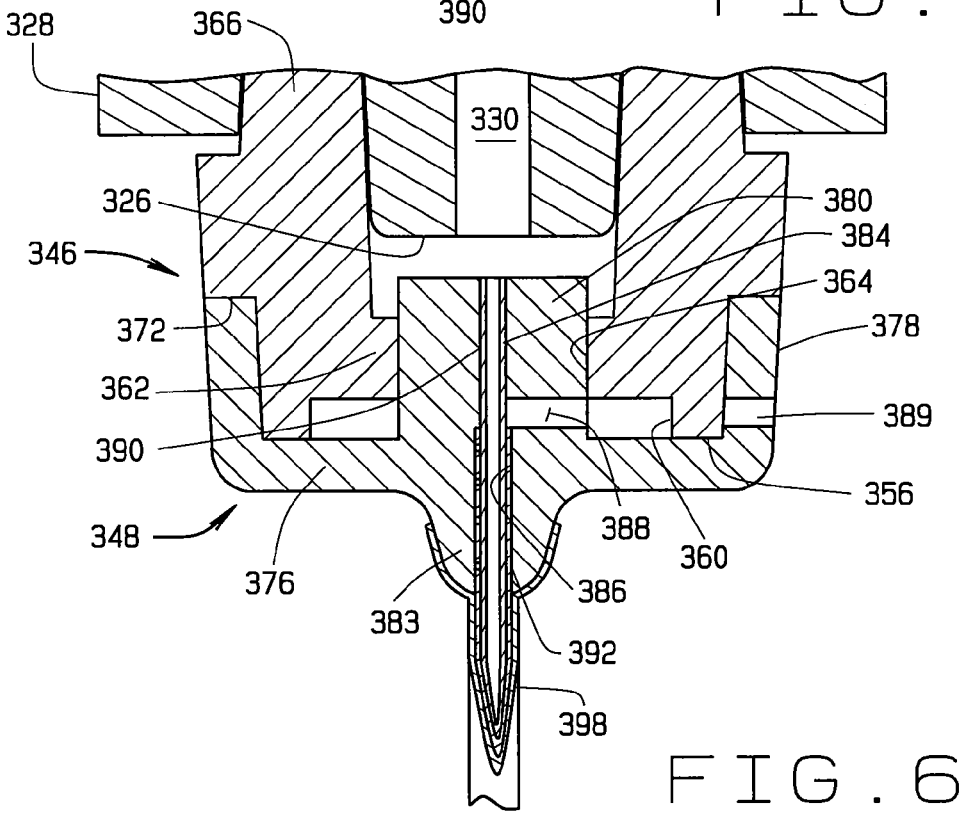
FIG. 6 is a cross-sectional view similar to that if FIG. 5, but taken 900 relative to FIG. 5.

A passage 384 (FIG. 6) extends through the post 380 and projection 383. An axial counter-bore 386 is formed in the passage 384 and extends upwardly from the bottom of the projection 383, giving the passage 384 an upper section of one diameter and a lower section of a second, larger diameter. A lateral bore 388 extends from the passage 384 outwardly to the surface of the post 380. The lateral bore 388 is positioned just above the upper end of the bore 386, and the axial bore 386 opens into the lateral bore 388. Hence, the bore 386 is in communication with the annular channel 382 by way of the lateral bore 388. An opening 389 is shown in the cover peripheral wall 378. The opening 389 is aligned with the lateral bore 388, and is made during the molding of the connector assembly cover 348. The opening or passage 389 (which as seen is closed when the cover 348 is mounted to the body 346) can be omitted.

The lumen 344 is fixed to the cover 348. The lumen 344 is a dual lumen and comprises two fluid passages. As shown in the drawings, the lumen 344 is a coaxial lumen and comprises an inner tube 390 and an outer tube 392. The inner tube 390 defines a central passage 394. As shown in FIG. 8, the outer tube 392 has an inner diameter slightly larger than the outer diameter of the inner tube 390, and the two tubes in combination define an annular outer passage 396.

The inner tube 390 is longer than the outer tube 392, and extends beyond both ends of the outer tube 392. The inner tube 390 has an outer diameter sized to be received in the connector cover passage 384. Similarly, the outer tube 392 has an outer diameter sized to be received in the cover axial bore 386. As seen in the drawings, the outer tube 392 extends to the top of the axial bore 386. Hence, the lumen outer passage 396 is in communication with the lateral bore 388. The inner tube 390 seals the passage 384 above the lateral bore 388, and thus, the lumen outer passage 396 is not in communication with the upper end of the passage 384.

Lastly, to seal the connector assembly 342, the projection 383 of the connector cover 348 and a portion of the outer tube 392 are covered by a sleeve 398. The sleeve 398 forms an air-tight seal at the junction of the lumen outer tube 392 and the connector cover 348.

To assemble the cannula assembly 340, the lumen 344 is inserted into the passage 384 and counter-bore 386 such that the lumen central passage 394 opens at the top of the cover post 380, and such that the lumen outer passage 396 is in communication with the lateral bore 388 of the cover 348. The sleeve 398 effectively fixes the lumen 344 to the cover 348 so that the lumen cannot be easily removed from the cover 348. Either before or after the lumen 344 is secured to the cover 348, the cover 348 is fixed to the connector assembly body 346. The connector assembly cover 348 can be fixed to the body 346 by any desired means, including gluing or welding. Additionally, the cover and body can be connected by physical means, such as a friction fit or a ball and detent connection.

As seen in the drawings, when the cannula assembly 340 is mounted to the irrigator/vacuum syringe 310, the lumen central passage 394 opens into the upper bore 358 in the connector body, and hence is in communication with the nose passage 330 and the waste chamber 324b. The lumen outer passage 396, on the other hand, opens into the connector cover lateral bore 388 which, in turn opens into the annular chamber 382 formed within the connector assembly 342. The connector assembly chamber 382, in turn, is in communication with the passage 368 in the connector body wall 366. The passage 368 opens into the annular channel 327 in the irrigator/vacuum syringe and hence, is in communication with the clean chamber 324a through the opening 332 in the bottom 318 of the irrigator/vacuum syringe. Hence, the lumen outer passage 396 is in fluid communication with the clean chamber 324a.

As can be appreciated, when a root canal is irrigated, the lumen needs to be sufficiently long to introduce the irrigating fluid into the root canal. However, when the spent, used or waste irrigating fluid entrained with elements of the smear layer is to be vacuumed from the canal, the vacuuming lumen preferably reaches far down into the root canal, and preferably within 1-2 mm of the working length of the canal. Hence, for this reason, the inner tube 390 which is in communication with the waste chamber 324b is longer than the outer tube 392. Further, the inner tube 390 has an outer diameter that is sized to fit easily within the diameter of the fully prepared and tapered root canal preparation. To this end, the inner tube 390 has an outer diameter of about 0.2 mm. As can be appreciated, the lumen outer tube 392 has a diameter that can be inserted into a root canal, but need not be so narrow as to reach to the end of the root canal. As noted, the outer lumen tube 392 is preferably shorter than the inner lumen tube 390, and is sized such that the outer lumen tube will extend about one-half to two-thirds of the overall length of the root canal. One of ordinary skill in the art would know that in order for the lumen to navigate around bends and curves in the root canals of a tooth and to reach substantially to the end of the root canal, as noted above, the lumen will have to be flexible. When the cannula is used, irrigant will be injected into the root canal along the body of the root canal. When the practitioner vacuums using the irrigation/vacuum device (such as disclosed in co-pending application Ser. No. 11/618,191 which is incorporated herein by reference), the irrigant will be pulled down to the bottom of the canal by reason of the inner (vacuum) lumen tube 390 being longer than the outer (irrigation) lumen tube 392. Having the entrance for the vacuum lumen tube displaced relative to the exit from the irrigation lumen tube helps circulate the irrigant within the root canal. Although it is preferred that the vacuum tube be the longer of the two tubes, it will be appreciated that the exit from the irrigation tube will be spaced below the entrance to the vacuum tube. Further, the two tubes can be of the same length—that is, the entrance to the vacuum tube can be at the same level as the exit from the irrigation tube.

The outer passage 396 can be opened only at the end of the outer tube 392. This will effectively introduce irrigating fluid into the root canal at a particular level within the root canal. However, the outer tube 392 can be provided with pores 400 in the tube wall to allow for fluid to pass out of the side wall of the tube. This will allow for the introduction of irrigating fluid into the root canal along a length of the root canal, rather than at a particular level within the root canal. If pores 400 are provided, the end of the outer tube 392 can be sealed against the inner tube, such that the outer passage 396 will not exit the outer tube 392 at the base of the outer tube.

The lumen 344 is shown in FIGS. 4-8 to be a coaxial dual lumen. However, the lumen can also be a side-by-side dual lumen. As shown in FIG. 9, the lumen 344' includes tubes 390' and 392' which define passages 394' and 396'. The tubes 390' and 392' are shown in a side-by-side relationship and are held together by a web 393.

The cannula assembly is illustratively described above with the vacuum-tube being the inner tube 390 of the cannula and the irrigation tube is the outer tube 392; and that the vacuum-tube is longer than the irrigation tube. However, one skilled in the art will appreciate that the positions of the two tubes could be reversed such that the irrigation tube is the inner tube and the vacuum tube is the outer tube. Further, it will be appreciated that the vacuum and irrigation tubes can be of the same length, or the irrigation tube could be longer than the vacuum tube.

Figures 11A, 11B, 11C:
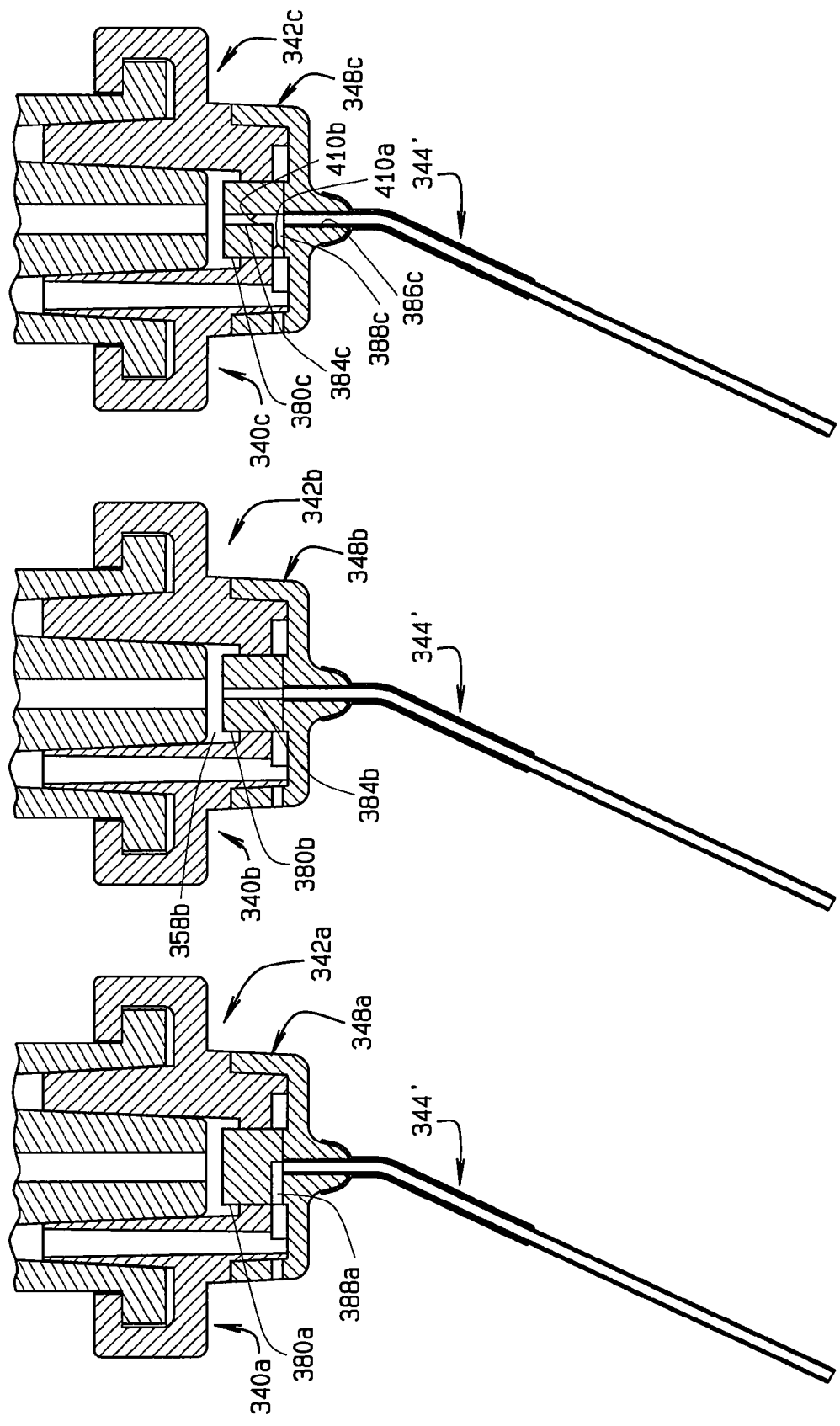
FIGS. 11A-C are cross-sectional views showing three variations of the cannula assembly comprising a single tube lumen wherein the cannula assembly is designed for an irrigation only mode (FIG. 11A), a vacuum only mode (FIG. 11B), and a combined irrigation and vacuum mode (FIG. 11C).

Often during preparation of a root canal, a practitioner will want to flush or irrigate the canal as it is then prepared. However, the canal, at that point, may not be sufficiently wide enough to receive a dual lumen cannula, such as shown and described above. As such, the practitioner, at that point, may want to work in an irrigation only mode. Hence, the practitioner can use a single-lumen cannula assembly 340a as illustratively shown in FIG. 11A. This cannula assembly 340a is substantially similar to the cannula assembly 340 of FIGS. 1-6. However, as seen in FIG. 11A, the central post 380a is solid, and there is no upper bore similar to the upper bore 384 of the cannula assembly 340. Additionally, the lumen 344' is a single lumen comprised of a single tube which extends into the connector assembly 342a to open into, and communicate with the lateral bore 388a in the connector cover 348a. With the upper bore 384 having been eliminated, the cannula assembly 340a can operate only in an irrigation mode.

Often during preparation of a root canal, a practitioner will want to operate in a vacuum only mode. Depending on the size of the preparation, the canal may not be sufficiently wide enough to receive a dual lumen cannula. The practitioner can use a single-lumen cannula assembly 340b as illustratively shown in FIG. 11B. This cannula assembly 340b is substantially similar to the cannula assembly 340 of FIGS. 1-6. However, as seen in FIG. 11B, the central post 380b has been modified to eliminate that lateral bore 388, such that there is only the upper bore 384b. In the connector 340b, the single tube lumen 344' communicates the chamber 358b by way of the upper bore 384b, and in this manner is in communication with the waste chamber 324b as can be seen from FIG. 1.

Finally, and again due to various circumstances, a practitioner may want to use a single tube lumen which can be used to both vacuum and irrigate. The practitioner can use a single-lumen cannula assembly 340c as illustratively shown in FIG. 11C. This cannula assembly 340c is substantially similar to the cannula assembly 340 of FIGS. 1-6. Unlike the cannula assemblies 340a and 340b, the central post 380c includes both the lateral bore 388c and the upper bore 384c. The cannula assembly 340c differs from the cannula assembly 340 in that the single tube lumen 344' extends through the lower bore 386c such that the lumen tube is in communication with both the lateral bore 388c and the upper bore 384c. Hence, the single lumen tube is in communication with both the clean chamber and waste chamber. As discussed in co-pending application Ser. No. 11/618,191, which was published as US2008-0160479, and which is incorporated herein by reference, the syringe when in a irrigation/vacuum mode will force fluid out the clean chamber 324a of the syringe 310 when the plunger of the pump assembly 314 is compressed, and will suck waste fluid into the waste chamber 324b of the syringe with the plunger is released. With the lumen 314' in communication with both the clean and waste chambers of the syringe via the bores 384c and 388c, waste fluid might enter the clean chamber during a vacuum. To prevent waste fluid from being released from the waste chamber 324b and to prevent waste fluid from being pulled into the clean chamber 324a, one-way valves 410a,b in the bores or passages 388c and 384c respectively. The valves 410a,b can be spring biased ball or disc valves, duckbilled valves, or any other type of one-way valve. The one-way valve 410a in the bore or passage 388c allows fluid to flow toward the lumen 344' from the clean chamber, but does not allow fluid to flow through the bore 388c from the lumen 344'; and the one-way valve 410b in the bore or passage 384c allows fluid to flow up from the lumen, but does not allow fluid to flow down (relative to FIG. 11C) from the waste chamber 324b.

The anatomy of the root canals in the teeth of a single patient will vary, depending on the tooth being worked on. Additionally the length, diameter, and curvature of any given canal will vary from patient to patient. Hence, the cannula assemblies 340, 340' will preferably be provided in different diameters and different lengths. For example, the dual cannula assemblies can be provided in small, medium and large sizes wherein the length of the vacuum tube for each is, for example 21 mm, 25 mm, and 31 mm, respectively, and the overall diameter of the cannula assemblies are, for example, 0.3 mm, 0.5 mm, 0.7 mm, respectively. Similarly, the single lumen cannula assembly can be provided in small, medium and large sizes wherein the lengths of the lumens for each is, for example 21 mm, 25 mm and 31 mm, respectively, and the diameter of each is, for example, 0.3 mm, 0.5 mm, 0.7 mm, respectively. Of course, these sizes can be changed as desired to have different length or different diameter tubes. By providing a single lumen cannula assembly in addition to a dual lumen cannula assembly, the practitioner is given the choice of cannulas to use at a given point in the procedure without the need to switch syringe bodies. Hence, the practitioner is provided with the option of single and dual lumen cannula assemblies each of which can be provided in different lengths and/or diameters.

In an endodontic (i.e., root canal) procedure, for example, the practitioner begins the procedure by preparing an endodontic access cavity to the pulp chamber. When an orifice has been identified, then this canal can be initially negotiated in preparation for cleaning and shaping procedures. During the early phase of root canal preparation, the canal may be too small for the dual lumen cannula of FIGS. 1-6, and hence, the practitioner may choose instead to use one of the single lumen cannula of FIGS. 11A-C. Further, during this portion of the procedure, gross (as opposed to fine) shaping of the canal is performed, and the practitioner will liberally irrigate the preparation with solution to keep fresh solution flowing through the canal as it is prepared and to force out gross debris (bits of dentin, etc) from the preparation. The tooth debris that is formed may be too large for the vacuum tube of either the dual or single lumen cannulas. Hence, the practitioner may prefer to use the syringe in an irrigation only mode. In this instance, the practitioner's assistant will operate a separate vacuum device, as is know, to remove the excess fluid that is flushed from the preparation and the debris that is formed during the early preparation of the canal when significantly more debris is generated.

After the preparation has been completed, the practitioner can begin to more definitively clean the root canal system (i.e. improve debridement, removal of the smear layer, and disruption of the bio-film layer). During this portion of the procedure, the debris that is removed is sufficiently small to be vacuumed through the lumen of the cannula. Hence, the practitioner may want to use the syringe in a combined irrigate and vacuum mode, so that for each injection of solution into the canal, some of the used solution (in which the smear layer and bio-film constituents are suspended) will be removed from the canal. Depending on the size of the preparation, the practitioner can choose to use either the dual lumen cannula assembly 340 or one of single lumen cannula assemblies.

Finally, when the practitioner is ready to remove excess moisture from the prepared canal to dry the canal in preparation for filling and sealing the canal, or to change solutions, the practitioner may want to use the syringe in a vacuum only mode. Again, depending on the size of the canal preparation, the practitioner can use either the dual lumen cannula assembly or one of the single lumen cannula assemblies which allow for vacuuming of solution from the canal.

As various changes could be made in the above constructions without departing from the scope of the invention, it is intended that all matter contained in the above description or shown in the accompanying drawings shall be interpreted as illustrative and not in a limiting sense. Although the connector assembly 342 is shown to comprise two pieces, namely the connector body 346 and the connector cover 348, the connector assembly 342 could be formed as a unitary, one-piece element. The connector cover 348 could be adapted to receive a side-by-side dual lumen, rather than a co-axial dual lumen, for example, by shaping the counter-bore 386 to receive the side-by-side lumen 344'. These examples are merely illustrative.

The invention claimed is:

1. A cannula assembly which is removably connectable to a dental irrigator/vacuum syringe; the cannula assembly comprising a single connector and a lumen;

said single connector being adapted to be removably connected to a dental irrigator/vacuum syringe, the connector defining:

an upper end, a side wall and a lower end; and a waste fluid flow path and a fresh fluid flow path; said waste and fresh fluid flow paths both opening at said connector upper end; said waste and fresh fluid flow paths both extending through said single connector from said upper end of said connector toward said lower end of said connector; said waste and fluid flow paths being at least in part separate from each other; and said lumen being a one-piece lumen having a fixed end and a free end remote from said fixed end; said fixed end being fixed to said lower end of said single connector and extending from said single connector lower end; said fixed end of said lumen being spaced axially from said upper end of said single connector whereby said lumen is placed in communication with said syringe by way of said single connector; said one-piece lumen defining a lumen vacuum tube and a lumen irrigation tube; said lumen vacuum tube being in communication with said waste fluid flow path defined by said single connector and said lumen irrigation tube being in communication with said fresh fluid flow path defined by said single connector; said vacuum tube having an exit proximate said fixed end of said lumen and said lumen irrigation tube having an entrance proximate said fixed end of said lumen; said lumen being adapted to reach to within 1-2 mm of the working length of the root canal; said lumen irrigation tube being of a length such that fresh fluid will be delivered directly into the root canal under pressure.

2. The cannula assembly of claim 1 wherein said lumen irrigation tube has an exit proximate said free end of said lumen and spaced from said connector and wherein said lumen vacuum tube has an entrance proximate said free end of said lumen and spaced from said connector; said lumen irrigation tube exit allowing fluid to exit from said cannula assembly and said lumen vacuum tube entrance allowing fluid to enter said cannula assembly.

3. The cannula assembly of claim 2 wherein said lumen vacuum tube and lumen irrigation tube are coaxial; said lumen vacuum tube defining an inner passage and said lumen irrigation tube defining an outer passage.

4. The cannula assembly of claim 2 wherein said vacuum tube entrance and said irrigation tube exit are spaced axially from each other.

5. The cannula assembly of claim 4 wherein said lumen vacuum tube is longer than said lumen irrigation tube; said entrance being at an end of said lumen vacuum tube and said exit being at an end of said lumen irrigation tube; said lumen vacuum tube entrance being spaced below said lumen irrigation tube exit.

6. The cannula assembly of claim 5 wherein said lumen irrigation tube has a plurality of exit pores on a wall of said irrigation tube.

7. The cannula assembly of claim 6 wherein said lumen irrigation tube is sealed at a bottom thereof, such that fluid can only exit said irrigation tube through said pores.

8. A cannula assembly which is removably connectable to a dental irrigator/vacuum syringe; the cannula assembly comprising a connector and a lumen;
   said connector being adapted to be removably connected to a dental irrigator/vacuum syringe, the connector defining:
      an upper surface, a side wall and a lower surface; and
      a waste fluid flow path and a fresh fluid flow path; said waste and fresh fluid flow paths both extending from said connector upper surface and opening at said connector upper surface, and being at least in part separate from each other; and
   wherein said fresh fluid flow path of the connector comprises a first connector passage and said waste fluid flow path of the connector comprises a second connector passage; said first connector passage and second connector passage being generally parallel to each other; said first connector passage being longer than said second connector passage; said connector further comprising an axial connector passage extending from the connector lower surface; said axial connector passage comprising an upper portion which opens into said second connector passage and a lower portion; said connector further including a laterally extending bore extending between said first connector passage and said axial connector passage to place said lower portion of said axial connector passage in communication with said first connector passage;
   said lumen being fixed to and extending from said connector; said lumen defining a lumen vacuum tube which is placed in communication with said waste fluid flow path defined by said connector and a lumen irrigation tube which is placed in communication with said fresh fluid flow path defined by said connector; said lumen irrigation tube being separate from said lumen vacuum tube; said lumen being adapted to reach to within 1-2 mm of the working length of the root canal; said lumen irrigation tube being of a length such that fresh fluid will be delivered directly into the root canal under pressure.

9. The cannula assembly of claim 8 wherein said connector comprises a connector body and a connector cover;
   said connector body having an upper surface and a lower surface; said connector body upper surface defining said connector upper surface; said connector body comprising a bore in said connector body lower surface and an opening in a top surface of said bore placing said bore in communication with said second connector passage; said first connector passage extending through a wall of said connector body from said connector body upper surface to said connector body lower surface;
   said connector cover comprising said connector lower surface, a cover peripheral wall extending around said connector lower surface, and a cover post extending upwardly from said connector lower surface; said axial connector passage extending through said post; said laterally extending bore extending from a surface of said post to said axial connector passage in said cover post.

10. The cannula assembly of claim 9 wherein said cover post and connector body bottom bore in combination define an annular chamber; said first connector passage being in communication with said annular chamber.

11. A cannula assembly which is removably connectable to a dental irrigator/vacuum syringe; the cannula assembly comprising:
   a connector assembly comprising
      a connector body; said connector body comprising:
         an upper surface and a lower surface;
         a first passage extending downwardly from said upper surface, said first passage extending from said connector body upper surface to said connector body lower surface;
         a second passage; said second passage being generally parallel to said first passage and having a length less than the height of said connector body;
         a bottom bore in said connector body lower surface, said bottom bore being generally aligned with said second passage; said first passage opening into said bottom bore; and
         an opening in said bottom bore, placing said bottom bore in communication with said second passage; and
      a connector cover; said connector cover comprising
         a peripheral side wall sized and shaped to be mated with said connector body;
         a bottom wall;
         a cover post extending upwardly from said connector cover bottom wall; said cover post being positioned to be aligned with said opening in said bottom bore of said connector body; said cover post being sized to extend into said bottom bore opening and shaped to be snuggly received in said bottom bore opening; said cover post and connector body bottom bore, in combination defining an annular channel;

an axial passage extending generally axially through said cover post, said axial passage having an upper portion and a lower portion; and
a lateral bore extending from a side of said cover post to said axial passage; and
a lumen connected to and extending from said connector cover; said lumen being received in said connector cover axial passage and being in communication with at least one of said axial passage and said lateral bore of said post.

12. The cannula assembly of claim 11 wherein said lumen comprises a single tube lumen; said single tube lumen being in communication with both said axial passage and said lateral bore of said post; said connector assembly further comprising one-way valves in said axial passage and said lateral bore of said post; the one-way valve in the lateral bore only permitting fluid to flow toward said lumen and the one-way valve in the axial passage only permitting fluid to flow from said lumen.

13. The cannula assembly of claim 11 wherein said lumen comprises a first tube defining a first lumen passage and a second tube defining a second lumen passage; said lumen second tube extending into said upper portion of said axial passage such that said second lumen passage is in fluid communication with said connector body second passage; and said lumen first tube extending no further than said lateral bore such that said lumen first passage is in communication with said lateral bore, and hence said connector body first passage.

14. The cannula assembly of claim 13 wherein said lumen second tube extends beyond an end of said lumen first tube.

15. The cannula assembly of claim 13 wherein said lumen first tube includes a plurality of pores formed in a wall of said first tube; said pores defining exit ports for solution passing through said first tube.

16. The cannula assembly of claim 15 wherein said lumen first tube is closed at a distal end of said first tube.

17. The cannula assembly of claim 11 wherein said connector body second passage is generally centered relative to said cover body; said cover body having an annular wall; said connector body first passage extending through said annular wall.

18. The cannula assembly of claim 11 wherein said cover axial passage is generally centered and generally aligned with said connector body second passage; said axial passage including an upper portion and a lower portion; said upper portion extending upwardly from said lateral bore; said lower portion of said axial passage having a diameter greater than said upper portion of said axial passage.

19. The cannula assembly of claim 18 wherein said lumen is a coaxial dual lumen comprising a first tube and a second tube; said lumen second tube defining a central passage and said lumen first tube defining an outer passage; said lumen second tube extending above a top end of said first tube.

20. The cannula assembly of claim 19 wherein said lumen second tube has a diameter sized to be received in said upper portion of said axial passage and to effectively seal against a wall of said upper portion of said axial passage.

21. In combination, a combined dental irrigator/vacuum syringe and a cannula removably mountable to said irrigator/vacuum syringe;
said irrigator/vacuum syringe comprising a hollow syringe body having a body bottom and defining a first chamber and a separate second chamber; there being a first chamber opening in said syringe body bottom in said first chamber and a second chamber opening in syringe body bottom in said second chamber; said first and second chamber openings being spaced apart from each other;
said cannula comprising
a connector, the connector comprising
an upper surface, a side wall and a lower surface;
a first connector passage and a second connector passage; said first and second connector passages both extending from said connector upper surface and opening at said connector upper surface; said first and second connector passages each having an upper end and a lower end, said upper ends of said passages being at said connector upper surface;
an axial connector passage in said connector lower surface; said axial connector passage having an upper end and a lower end; said axial connector upper end being spaced axially above said lower end of said first connector passage; said axial connector passage being in communication with said first and second connector passages; and
a flexible lumen fixed to and extending from said connector; said lumen being received only in said axial connector passage; said lumen being in communication with one or both of said first connector passage and said second connector passage; whereby, when said cannula is mounted to said irrigator/vacuum syringe, said lumen is in communication with one or both of said syringe body first chamber and said syringe body second chamber.

22. The combination of claim 21 wherein said lumen is a single tube lumen comprising a single tube received in said connector lower surface.

23. The combination of claim 22 wherein said single tube is in communication with said first connector passage by way of said axial connector passage and with said second connector passage.

24. The combination of claim 23 and further including a first one-way valve in one of said axial connector passage and said first connector passage and a second one-way valve in said second connector passage; said first one-way valve permitting the flow of fluid in only a first direction and the second one-way valve permitting the flow of fluid in only a second direction opposite of said first direction.

25. The combination of claim 21 wherein said lumen is a dual tube lumen and comprises a first tube defining a first lumen passage and a second tube defining a second lumen passage; said first lumen passage being in fluid communication with said first connector passage and said second lumen passage being in fluid communication with said second connector passage.

26. The combination of claim 21 wherein said irrigator/vacuum syringe includes a nose extending from said body bottom and a collar surrounding said nose; said nose and collar defining an annular channel; said nose being generally centered relative to said body bottom and including a passage therethrough; said nose passage defining said first chamber opening; said second chamber opening being positioned in said body bottom between said nose and said collar;
said second connector passage being defined by an annular wall sized and shaped to fit about said syringe nose and to be received in said syringe annular channel; said first connector passage extending through said connector annular wall.

27. The combination of claim 26 wherein said first and second connector passages are generally parallel to each other; said first connector passage being longer than said second connector passage; said axial connector passage comprising an upper portion which opens into said second connector passage and a lower portion; said connector further including a laterally extending bore extending between said first connector passage and said axial connector passage to place said lower portion of said axial connector passage in communication with said first connector passage.

28. The combination of claim 27 wherein said a lateral bore extends between said first connector passage and said lower portion of said axial connector passage; said lumen being a dual tube lumen comprising a first tube and a second tube, said first tube extending into said upper portion of said axial connector passage such that said lumen second passage is in fluid communication with said connector body second passage; and said lumen first tube extending no further than said lateral bore such that said lumen first passage is in communication with said lateral bore, and hence said connector body first passage.

* * * * *